(12) United States Patent
Jansen et al.

(10) Patent No.: US 8,709,501 B1
(45) Date of Patent: Apr. 29, 2014

(54) METHOD FOR TREATING WOUNDS FOR MAMMALS, WOUND HEALER COMPOUND, AND METHOD OF MANUFACTURING THEREOF

(76) Inventors: Beverly Jansen, Tamarac, FL (US); Tania E. Toney-Parker, Wadmalaw Island, SC (US); Donna Webber, Port St. Lucie, FL (US)

( * ) Notice: Subject to any disclaimer, the term of this patent is extended or adjusted under 35 U.S.C. 154(b) by 0 days.

(21) Appl. No.: 13/554,684

(22) Filed: Jul. 20, 2012

Related U.S. Application Data (60) Provisional application No. 61/510,558, filed on Jul. 22, 2011.

(51) Int. Cl.
 *A61K 33/04* (2006.01)
 *A61K 36/185* (2006.01)
 *A61K 36/28* (2006.01)

(52) U.S. Cl.
 USPC .......................... 424/714; 424/725; 424/764

(58) Field of Classification Search
 USPC .......................................... 424/714, 725, 764
 See application file for complete search history.

(56) References Cited

U.S. PATENT DOCUMENTS

| | | | | |
|---|---|---|---|---|
| 5,266,330 A * | 11/1993 | Cannon | ........................ | 424/445 |
| 7,959,955 B1 * | 6/2011 | Manickam | .................... | 424/725 |
| 8,221,802 B2 * | 7/2012 | Manickam | .................... | 424/725 |
| 2005/0074414 A1 * | 4/2005 | Tamarkin et al. | ............... | 424/47 |
| 2008/0038377 A1 * | 2/2008 | Citow | ........................... | 424/725 |
| 2008/0279902 A1 * | 11/2008 | Luria et al. | .................... | 424/401 |
| 2012/0034323 A1 * | 2/2012 | Doherty et al. | ............... | 424/727 |

FOREIGN PATENT DOCUMENTS

| | | | | |
|---|---|---|---|---|
| EP | 0424534 A1 * | 5/1991 | ............. | A61K 35/78 |
| RU | 2000805 C1 * | 10/1993 | ............. | A61K 35/78 |
| RU | 2366432 C1 * | 9/2009 | ............. | A61K 33/04 |
| WO | WO 03/088985 A2 * | 10/2003 | ............. | A61K 36/28 |
| WO | WO 2004/035071 A1 * | 4/2004 | ............. | A61K 35/78 |

* cited by examiner

*Primary Examiner* — Aradhana Sasan
(74) *Attorney, Agent, or Firm* — H. John Rizvi; Gold & Rizvi, P.A.

(57) ABSTRACT

A composition and method of use for treating wounds of mammals comprising an effective amount of the plant extracts *Calendula officinalis* and sublimed sulfur in a topical pharmaceutical carrier and or tea tree oil. The unique combination of these active plant extracts treats any type of wound effectively and immediately by increasing granulation at the site of the wound, promoting metabolism of proteins and collagen, inducing new cell growth, stopping bleeding, minimizing pain, and providing anti-bacterial activity. The present invention also provides a *calendula* composition to be administered orally to a mammal to alleviate EIPH or bleeding. The present invention also provides a *calendula* composition to alleviate the negative effects of inflammation due to stress, to treat muscle pulls and joints, to improve the eating regimen of high performance mammals, to treat mastitis, anhydrosis, and treat or prevent an ulcer in the stomach or duodenum of a mammalian patient.

14 Claims, 5 Drawing Sheets

METHOD FOR TREATING WOUNDS FOR MAMMALS, WOUND HEALER COMPOUND, AND METHOD OF MANUFACTURING THEREOF

CROSS-REFERENCE TO RELATED APPLICATIONS

This application claims the benefit of U.S. Provisional Application No. 61/510,558, filed Jul. 22, 2011 and entitled METHOD FOR TREATING WOUNDS FOR MAMMALS, WOUND HEALER COMPOUND, AND METHOD OF MANUFACTURING THEREOF, which provisional application is incorporated by reference herein in its entirety.

BACKGROUND OF THE INVENTION

1. Field of the Invention

The present invention relates generally to a method for treating wounds, inflammation, exercise induced pulmonary hemorrhage (EIPH), pain, ulcers or hypersecretion, loss of appetite, anhydrosis and bleeding for mammals using an effective amount of plant extracts, e.g., *Calendula officinalis*, and or sublimed sulfur or flowers of sulfur and or Gentian and or chamomile and or Tea Tree Oil and the like in a topical or oral pharmaceutical carrier selected from the group consisting of ointments, lotions, solutions, suspensions, capsules, pastes, solvents, gels, sprays or aerosols. The invention is, however, more particularly directed to a method for treating multiple types of wounds for mammals, a wound healer compound used during the healing process, and the method of manufacturing said compound.

2. Description of the Prior Art

Slow or improper wound healing may compromise the quality of life of a mammal and/or lead to infection. There are several products in the prior art to address this issue but most of them have the tendency to keep the wound too moist which sometimes leave them more susceptible to infections. Furthermore, it takes much longer for these products to heal the wound.

The *calendula* flower is known to possess unique properties and assist in wound healing, reduce inflammation, soothe and soften skin and assist in the rejuvenation of the cell. The structural isolation and identification of active ingredients comprising the *calendula* extract have yet to be identified. Calendula has been used for centuries as a homeopathic remedy. Historically, it has traditionally been used to treat the following conditions: abscesses, acne, anemia, anxiety, appetite stimulant, athlete's foot, bacterial infections, bladder irritation, blood purification, bowel irritation, bruises, cholera, circulation problems, conjunctivitis, constipation, contact dermatitis, cramps, diaper rash, dizziness, gingivitis, gout, gum disease treatment and prevention, hemorrhoids, herpes simplex virus infections, HIV, indigestion, influenza, insomnia, jaundice, menstrual period abnormalities, mouth and throat infections, ringing in the ears, sore throat, spasms, stomach ulcers, uterus problems, varicose veins, warts and yeast infections.

Human clinical studies have been conducted that provided scientific evidence that *calendula* can be utilized for various skin conditions such as hard to heal wounds, thermal and radiation burns, stings, diaper rash and contact dermatitis. A small study in caesarian patients supports the use of *calendula* in helping heal surgical wounds. This study demonstrated that *calendula* sped up the wound-healing process by increasing blood flow to the affected area and promoting the production of collagen proteins. In addition, another study investigated the relationship between the beneficial properties of *calendula* extract and its antioxidant properties; the results obtained suggested that the butanolic fraction of *Calendula officinalis* demonstrated a significant free radical scavenging and antioxidant activity. In France, a study was conducted to assess the prevention of dermatitis in 250 women patients having radiation therapy for breast cancer; the result indicated that there was significantly less pain from the radiation for the women using *calendula*.

Flowers of sulfur or sublimed sulfur are a sulfur powder that is a very popular ingredient in herbal remedies around the world. It was used since ancient times as a laxative, antiseptic and disinfectant. It is used in prescription compounding for various skin disorders. Until the seventeenth century, it was also used as a diuretic in dropsy, a drastic in diarrhea, a drastic for dysentery and suppression of urine, a laxative in gout and scurvy, an application to wounds, and corroborant for rheumatism.

Tea tree oil has historically been used in many conditions including the treatment of acne, apthous stomatitis, tinea pedis, boils, burns, carbuncles, corns, gingivitis, herpes, empyema, impetigo, infections of the nail bed, insect bites, lice, mouth ulcers, pharyngitis, psoriasis, root canal treatment, ringworm, sinus infections, skin and vaginal infections, thrush, and tonsillitis. As early as 1930, the antiseptic properties of the tea tree oil were recognized. Its therapeutic use as an antiseptic and antifungal agent is mainly known use today. Tea tree oil was selected for both its fragrance as well as its medicinal properties that are considered beneficial when applied topically which include antibacterial, antifungal, antiviral, and antiseptic properties. Tea tree oil also works well to minimize the sulfur odor that is present in the formulation.

Remedies, particularly herbal medications, are desired by consumers for the promotion of rapid and proper wound healing. For example, there is a medicated skin care preparation for promoting wound healing comprising at least two extracts selected from the group consisting of *calendula*, yarrow, wild rose, and plantain extracts.

Another known solution of the prior art comprises a method for treating human pressure ulcer conditions using an effective amount of the plant extract *Calendula officinalis* in a topical pharmaceutical carrier selected from the group consisting of ointments, lotions, pastes, solvents, jellies, sprays and aerosols.

Also known is a homeopathic formulation useful for treating pain and/or inflammation comprising tinctures and/or diluted extracts preferably subjected to potentiation of at least 8 or 9 herbs selected from *Bellis Perennis, Calendula officinalis, Hamamelis Virginiana, Arnica Montana, Hypericum Perforatum, Aconitum Napellus, Ledum Palustre, Bryonia Alba* and *Ruta Graveolens*.

Also known is the use of glycosidic compounds as pharmaceutical agents against psoriasis using purified plant active compounds of *calendula* for use in treating diseases involving the hyperproliferation of dermis cells.

Even though the above cited methods and compounds for treating wounds of the prior art address some of the needs of the market, a new, improved healing method for treating wounds is still desired.

In addition, to treating wounds, *calendula* can be effectively utilized orally to treat exercise-induced pulmonary hemorrhage (EIPH).

Exercise-induced pulmonary hemorrhage (EIPH) is a condition common to a large percentage of racing and maximally exercised animals. It is defined by the appearance of blood in the lungs of the animal as a result of a strenuous routine. A smaller percentage of these animals are commonly designated as bleeders once blood appears in the nostrils of the animal. This condition appears to be only symptomatic of the underlying source of the bleeding which originates as bleeding in the lungs of the animal.

It has been demonstrated that strenuous exercise, such as thoroughbred racing, competitive flat racing, pacing, trotting, jumping or barrel racing, can initiate a dramatic increase in the pulmonary capillary blood pressure that can result in the capillaries within the lung becoming abnormally permeable allowing the blood to enter the airways and hence, reduce the respiratory capacity of the lungs. The pulmonary hemorrhage can become so severe that the horse is unable to race and becomes of marginal value to both the breeder and racing circuit.

An understanding of equine physiology addresses why bleeding or exercise-induced pulmonary hemorrhage (EIP) is inevitable during a race. The tiny blood vessels in a horse's lungs rupture due to stress sustained during physical exertion. There are three known variations of EIPH: Simple EIPH, Patent Pulmonary Hemorrhage (PPH) and composite bleeding. Simple EIPH is an acute condition that results from the strain of exercise. PPH is a chronic condition that results in bleeding in the lungs due to hypertension, an infection or an allergen. Composite bleeding is a combined condition exhibiting the effects of both Simple EIPH and PPH. The effects of simple EIPH can heal naturally over several days whereas PPH has to be treated with various medications.

Simple EIPH occurs as a natural consequence of strenuous running due to the physiology of the horse's organs and the way the horse moves during high-speed galloping. The horse's body is divided into two parts. The front half of the horse's trunk contains the heart, lungs and other major organs. The back end of the horse contains the intestines suspended by ligaments within the abdomen. The two portions are separated by a thin sheet of muscle called the diaphragm. As the diaphragm contracts, the horse's front half or chest cavity increases in volume allowing air to fill the lungs. While running, the horse inhales as its front feet hit the ground and its skeletal structure is maximally stretched. As the horse's front feet leave the ground, the diaphragm relaxes, the skeletal structure compresses, the constricting chest cavity forces air out of the lungs, and the horse exhales.

As a result of the back and forth movement of high-speed galloping, the horse's intestines may swing like a pendulum. The motion of the intestines can get out of phase with the movement of the diaphragm, and the intestine moves forward as the horse tries to exhale. The diaphragm is slammed forward and upward and squeezes the lungs against the chest wall. The lungs are composed of alveoli, tiny air sacs, and capillaries, miniscule blood vessels. The alveoli and capillaries are so fine and interconnected. The inhaled air can pass oxygen to the bloodstream and carbon dioxide from the bloodstream to the lungs. Due to the repeated impact of the forward surge of the intestinal mass during the strenuous exercise, the fine capillaries rupture and clog the horse's air passages with blood. This creates breathing difficulties for the horse and impacts its ability to run. To even complicate this further, there are studies suggesting that air born debris, such as pollen and dust, can play a role in EIPH. The irritants can increase fluid and mucus or inflammation and lead to an obstruction of the horse's airways which lead to breathing difficulties during a race.

Virtually every horse that is required to gallop for prolonged periods is susceptible to the effects of simple EIPH. However, the problem is most notable in thoroughbreds due to the high speed required to be maintained for up to two minutes or more. Steeple-chasers, standardbreds, and heavy draft horses utilized in competition do not have to maintain the strenuous speed for prolonged duration and typically experience less severe bouts with EIPH. The incidence of EIPH ranges from about thirty percent for Standardbreds and polo ponies and greater than sixty percent for Thoroughbreds, Quarterhorses and Appaloosas. The minimum level of strenuous activity need to induce EIPH is unknown. EIPH has also been observed in some Thoroughbred horses only after trotting, cantering and slow training gallops.

All horses show at least some bleeding deep within the lungs when raced and can be medically treated for bleeding as a result. A trainer can have the horse examined with a bronchoscope after a race, and declared as a bleeder if blood is detected during a veterinary examination. As a result of the examination, the horse is declared a bleeder and permitted in the future to race with medication such as Lasix. Approximately two to three percent of thoroughbreds overtly bleed, and medical equipment is not necessary for detection. Many racehorses can be medicated as a preventative treatment.

The treatment and prevention of exercise-induced pulmonary hemorrhaging in non-human mammals is accomplished by the timely administration of a powerful diuretic, non-steroidal anti-inflammatory drug (NSAID), estrogens, atropine, coagulants, clenbuterol, ipratorium, cromolyn, intravenous saline, steam inhalation and or anti-inflammatory peptide analogs.

Diuretics have been utilized to attenuate pulmonary hemorrhage. The prophylactic method of choice today in North America, when approved by a race track, has been to inject furosemide, Lasix or Salix, to reduce or prevent such hemorrhage by depleting water and electrolyte and expelling the fluids in the urine. This results in the lowering of the horse's blood pressure, particularly the aorta and pulmonary artery. The reduce blood pressure in the capillaries is thought to mitigate the problem with EIPH.

Some experts believe that Lasix acts as a stimulant on some horses and enhances the performance of horses that normally could not have raced unless medicated. Experts also suggest that the sheer volume of fluid lost by a horse, up to twenty percent of the horse's weight, can impose an unfair weight advantage during a race when some horses are handicapped for as little as five to ten pounds. Furthermore, there are those that would suggest that a diuretic is administered to a horse to flush away any trace of an illicit performance-enhancing substance in the bloodstream.

However, furosemide is banned on race days in all other countries outside the United States and Canada. More than ninety percent of racing Thoroughbreds and fifty percent of racing Standardbreds in the US and Canada are dosed with furosemide a few hours before a race to prevent and treat bleeding. There is no conclusive evidence to suggest furosemide is actually effective in preventing or limiting bleeding in racehorses. The controversial treatment suggests that the drug may be used instead to enhance racing performance.

Butazolidin phenylbutazone (PBZ), is a non-steroidal anti-inflammatory drug (NSAID) that fights pain, inflammation and fever. It is typically utilized as a therapeutic drug to treat sick or injured horses. One side effect of NSAIDs is to decrease the platelet count in the bloodstream which results in the thinning of the blood. Some experts suggest that the thinning of the blood can exacerbate the problem with EIPH and cause ulcers and gastrointestinal irritation to horses. Butazolidin is used to numb a horse to pain of ailments, complete and even win a race. In most states, Butazolidin is the only other medication, besides Lasix, that is permitted in a horse's bloodstream during a race.

There is a need in the art for alternative treatments for exercise-induced pulmonary hemorrhaging in all mammals, specifically non-human mammals. The present invention overcomes the deficiencies of the prior art by providing a composition that consistently and reliably prevents and treats hemorrhaging in mammals.

In addition, this invention is also directed to the therapy of exercise-induced swelling of joints, and to alleviate the negative effects of muscle pulls, joint, tendon and ligament stresses, hematomas, and strains in mammals such as humans, horses and dogs. This therapeutic need is met using *Calendula officinalis*.

Mammals, such as humans, horses and dogs, are subjected to acute trauma during exercise whether it be for training, competitive events or for therapy. The average speed of racing Thoroughbreds is about 1050 meters per minute; racing greyhounds run average at fifteen miles per hour and human marathoners can run 26 miles in just over two hours. Such high speed will result in a high metabolic rate, a high respiration rate and stresses to articular areas. Even in mammals that are not fit an increased exercise that is far short of the speed of the athlete can result in wear and tear to the joints, resulting in swelling.

The continuous pounding of the leg joints results in acute swelling of the joint area. As a result of this type of trauma, tears in the blood vessels, ligaments and tendons surrounding the joint may be observed. This sequence of events results in edema, which is often accompanied by pain as the swollen tissues impinge on nerves or as a direct response to the cytokines released by the white blood cells.

The swelling can be relieved by various known methods. Generally, cold packs are applied when swelling is noted. This process is somewhat difficult, labor-intensive and may require specially designed packs to fit the mammal's joint. The swollen joint may be elevated to offer a benefit. It is well-known in the art to inject anti-inflammatory steroids such as prednisone directly into inflamed joints. However, steroid injection can result in arthropathy. In addition, oral steroids, aspirin and NSAID medication have also been recommended. Whatever the therapy, the mammal is generally allowed a rest period until the swelling diminishes.

The known methods are therapeutic and labor-intensive. The need remains for a composition that will decrease the length of time necessary reducing inflammation and pain associated with acute inflammation of mammalian body parts, particularly joints, due to injury or due to arthritic conditions or other disease conditions. This therapeutic need is met using Calendula.

The invention also includes a method of treating ulcers or hypersecretion and stress in an afflicted mammal which comprises administering to said mammal an effective amount of *calendula* and chamomile.

Each year, clinical mastitis afflicts 15% to 20% of cows in major milk-producing countries. It is documented that 50% of cows have one or more infected quarters in Canada and the United States. Using antibiotics is not an ideal solution. Antibiotics are not the ideal treatment for mastitis due to the problems they cause with the milk. These problems include withdrawal for several days, contamination from antibiotic residues, and problems associated with yogurt and cheese processing. Also, it is noted in the public domain, that there are problems associated with resistance or even ineffectiveness of antibiotics in the case of mastitis caused by coliforms and *Staphylococcus aureus*. In organic agriculture, the use of antibiotics is not an acceptable nor desirable alternative. The present invention is a solid alternative to the normally prescribed antibiotic treatment and can be used as a preventive and curative measure available to producers to deal with this problem.

The invention also includes a method for treating mastitis, acute clinical, hyperacute clinical, subacute clinical, chronic, gangrenous, contagious, environmental udder or intra-mammary infections which comprise administering to said mammal an effective amount of *calendula* and sulfur in an application where it is dosed (one syringe 10 mL) into each infected quarter immediately after the quarter has been completely milked out. If needed, repeat once only in 12 hours. Milk out udder completely. Wash the udder and teats thoroughly with warm water containing a suitable dairy antiseptic and dry preferably using individual paper towels. Carefully scrub the teat end and orifice with 70% alcohol using a separate swab for each teat. Allow to dry. Calendula gel can also be applied to the outside of the udder to reduce inflammation and provide comfort to the mammal while the mastitis is being treated.

The invention also includes a method for stimulating appetite in an afflicted mammal which comprises administering to said mammal an effective amount of calendula and Gentian.

The invention also includes a method for treating anhydrosis in an afflicted mammal which method comprises administering to said mammal an effective amount of calendula in an orally acceptable carrier with ascorbic acid, petroleum 6C and 30C, *Cinchona officinalis*, and 1-5% of all twelve cell salts consisting of *Calcarea fluorica, Calcarea phosphoric, Calcarea sulphurica, Ferrum phosphoricum, Kali muraiticum, Kali phosphoricum, Kali sulphurica, Magnesia phosphoric, Natrium muriaticum, Natrium phosphoricum, Natrium sulphuricum* and Silicea.

SUMMARY OF THE INVENTION

This invention is directed to a wound healer compound based on *calendula, Calendula officinalis*, sulphur and *calendula* cream, lard or *calendula*, sulfur and tea tree oil.

In one general aspect of the present invention, a method for treating wounds for mammals is described, which helps canine, camel, equine, goats, cows and livestock with their own ability to heal themselves more quickly.

Accordingly, it is a primary object of the present invention to provide a method for treating wounds for mammals, comprising the application of the product to the animal's wound to be thick enough so that the wound can no longer be seen.

Another aspect of the present invention provides a wound healer compound used during the healing process, comprising about 1 to 25% of the weight in *calendula* and 25% to 80% of the weight in sublimed sulfur in a topically acceptable carrier.

In summary, the present invention is related to a method for treating wounds for mammals using an effective amount of the plant extracts *Calendula officinalis* and sublimed sulfur or flowers of sulfur in a topical pharmaceutical carrier selected from the group consisting of ointments, lotions, pastes, solvents, gels, sprays or aerosols. The calendula is present by weight from about 1-25% and the sublimed sulfur is present by weight from about 40-60%.

These and other aspects, features, and advantages of the present invention will become more readily apparent from the attached drawings and the detailed description of the preferred embodiments, which follow.

The current invention is in relationship to a composition also used in the treatment for bleeding in mammals, particularly exercise-induced pulmonary hemorrhage (EIPH) in horses, camels and dogs. The composition comprises *calen-

*dula* and is formulated particularly for oral use but may also include other types of delivery systems to meet the therapeutic need described.

The current invention also teaches with various formulations containing *Calendula officinalis* as a means to treat inflammation, pain, ulcers or hypersecretion, anhydrosis and loss of appetite for mammals.

Homeopathic remedies for single component formulations of *calendula* and sulfur are known in the prior art as an aid in the treatment of skin conditions and employed in various forms for its germicidal, fungicidal and keratolytic actions. However, current applications do not teach the combination of the two agents to promote wound healing with an effective and immediate result. Furthermore, the current application does not teach the combination of the 2 agents with Tea Tree Oil to promote wound healing as well.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DETAILED DESCRIPTION OF REPRESENTATIVE EMBODIMENTS

Figure 1:
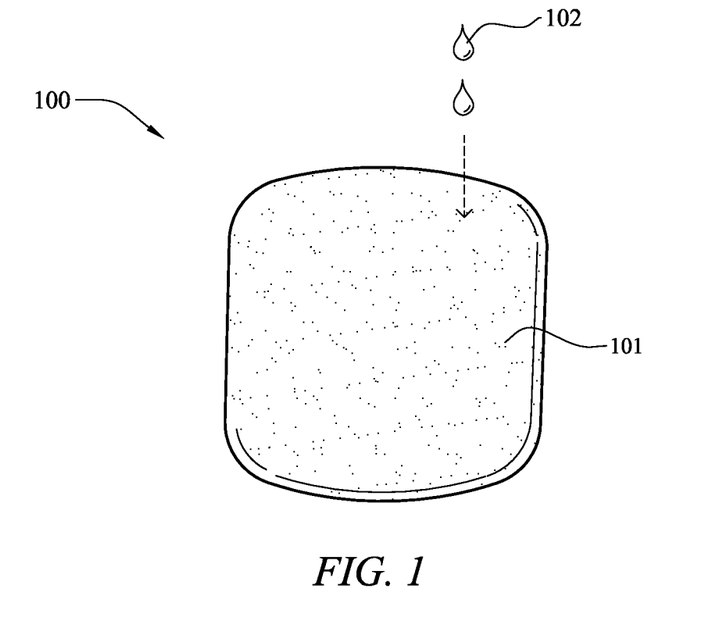
FIG. 1 is a general perspective view representative of the wound healing composition in accordance with an embodiment of the present invention.

A wound healing composition 100 is introduced in an exemplary representative illustration presented in FIG. 1. The wound healing composition 100 may be provided in a partially dehydrated state, wherein one or two drops of water 102 may be used to re-hydrate the wound healing composition 100 before applying it onto the wound as prescribed above.

DEFINITIONS

In the present specification, the following terms have the meaning specified below:

"Pharmaceutically acceptable" refers to entities, ingredients, and compositions that are physiologically tolerable and do not typically produce an allergic or similar untoward reaction when administered to an animal, particularly a human.

"Carrier" refers to, for example, a diluent, adjuvant, excipient, auxiliary agent or vehicle with which an active agent of a wound healing composition 100 is administered. Such pharmaceutically acceptable carriers can be sterile liquids. Water or aqueous saline solutions and aqueous dextrose and glycerol solutions may also be employed as carriers.

"Treatment or prevention of a condition" includes but is not limited to treatment or prevention of traumatic/chronic wounds; treatment and/or impediment to the progression of burns; treatment an eye condition; treatment or prevention of exercise-induced pulmonary hemorrhage; treatment or prevention of an ulcer in the stomach or duodenum of a mammalian patient; alleviating the negative effects of inflammation due to stress, bruises or cuts to ankles, tendons, shins or knees of a mammalian patient; improving the eating regimen of a mammal; treating mastitis, acute clinical, hyperacute clinical, subacute clinical, subclinical, chronic, gangrenous, contagious, environmental udder or intra-mammary infections in a mammalian patient or treating anhydrosis in a mammal.

Homeopathic remedies for single component formulations of *calendula* and sulfur are known in the prior art as an aid in the treatment of dermatitic conditions and employed in various forms for its germicidal, fungicidal and keratolytic actions. However, current applications do not teach the combination of the two agents to promote wound healing with an effective and immediate result. The wound healing composition 100 comprises a combination of extracts of *calendula* and sulfur that can be utilized for the treatment of all types of wound, including traumatic wounds and chronic wounds.

On-site animal studies have demonstrated that *calendula* in combination with sulfur appear to speed wound healing and possibly increase blood flow to the wounded site with the observance of an immediate scab to the wound and reduced healing time. Deep wounds on several equine adults required an initial treatment of 8.5% by weight of calendula extract in water with or without a preservative with sulfur powder applied directly on top of the freshly applied *calendula* extract preparation. After the first day of treatment, a thick layer of the gel preparation was applied to the wound. The active calendula sulfur preparation is not easily removed and adheres well to the wound. Other normal therapies had been tried on the equine subject and the vet and owner noted a failed response with typical treatments. After immediate application of the product, an immediate positive response was noted.

It was thought that a gelatinous network would provide a foundation to deliver both the *calendula* and sulfur to the wound while also providing a temporary skin to the wound as it heals. The preparation needed to be hydrophilic in nature, somewhat bioadhesive and the wound to be exposed to air and allow for the rapid healing process. The wound area should be allowed to air-dry following application. Bandages are not required, since the preparation itself forms a protective layer and is not easily removed by normal environmental conditions.

Carbomer 940 was selected for its gelling properties as well as for its ability to stand up to the incorporation of fragrances and essential oils within its gelatinous network when compared to other gelling agents. It would allow the tea tree oil to be incorporated into the formulation to mask the rotten egg smell from the high concentration of the sulfur present in the formulation.

In addition to the preferred gel base, various other gel base formulations can carry the active ingredients in the homeopathic formulations of the wound healing composition 100 with varying degrees of success. However, the use of glycerin, sulfur, calendula, tea tree oil in a water gel base of the preferred formulation is very emollient, non-drying, and soothing to the skin. Other carrier bases may also be used to deliver the active ingredients topically such as: water, alcohol, water/alcohol, cream ointment, salves, lotion, liniment, tinctures, cream gel, lotion ointment, rub, spray, aerosol, lotion spray, balm rub, gel ointment, lotion cream, poultice, plaster, infusion, decoction and other herbal methods of preparation. However, the gel delivery system does work best.

Glycerin or glycerol, which is a simple polyol compound, was included in the formulation to improve smoothness, provide lubrication and act as a humectant. Glycerol is also an effective treatment for psoriasis, burns, bites, cuts, rashes, bedsores, and calluses.

Preservatives were included in the formulation to inhibit mold, bacterial, and fungal growth.

The composition may further comprise a chelating agent, such as Ethylenediaminetetraacetic acid (EDTA) or Hydroxyethylenediaminetriacetic acid (HEDTA). The chelator generally comprises from about 0.020% to about 2.0%, preferably about 0.05% to about 1.5%, more preferably about 0.1% to about 1.0% by weight of the composition of the wound healing composition 100.

The pharmaceutical composition of the wound healing composition 100 is effective at pH values between pH 4 and pH 9. Preferably, the pH of the composition is between the following pH ranges: about 5.5 and about 6.5, about 4 to about 9, about 4 to about 8, about 4 to about 7, about 5 to about 9, about 5 to about 8, about 5 to about 7. Most preferably, the pH is about 6. One of ordinary skills in the art may add appropriate pH adjusting ingredients to the wound healing composition 100 to adjust the pH to an acceptable range. One example of such a pH adjusting agent is an amino, such as triethanolamine, sodium hydroxide or potassium hydroxide.

The wound healing composition 100 may be in a variety of forms, including lotions, creams, gels, sticks, sprays, mousses, emollients, ointments, pastes, and the like. These product types may comprise several types of formulations including, but not limited to solutions, emulsions, gels, solids, and liposomes.

The pharmaceutical compositions for ulcers are usually administered as a mixture with a carrier suitably selected depending upon the route for administration using standard formulations. Suitable compositions may take the form of a solution, suspension, tablet, coated tablet or any pharmaceutically acceptable form suitable for delivery to the stomach or duodenum.

For example, the compound of the present invention may be administered in the form of tablets which may be prepared using known techniques by adding to a powder of the active ingredient of the present invention an excipient such as starch, lactose, sucrose, glucose, crystalline cellulose, calcium carbonate or kaolin, a hydroxypropylcellulose, a glucose solution, a sucrose solution, water or ethanol, a disintegrator such as starch, agar, gelatin powder, carboxymethylcellulose calcium (CMC-Ca), carboxymethylcellulose sodium (CMC-Na), crystalline cellulose, calcium carbonate or sodium hydrogencarbonate, or a lubricant such as magnesium stearate, calcium stearate, talc, macrogoal 4,000, macrogoal 6,000 or stearic acid.

The mixture is then subjected to compression molding by a conventional tableting method, and if necessary, applying a sugar coating by means of a concentrated sugar solution containing e.g. gum arabic, talc, polyvinylpyrrolidone, polyethyleneglycol and/or titanium oxide, applying a film coating by means of a film-forming agent composed of e.g. polyvinyl acetal diethylaminoacetate, hydroxypropylmethylcellulose, hydroxypropylcellulose, ethylcellulose or polyvinylpyrrolidone or applying an enteric coating by means of a film-forming agent composed of e.g. ethylcellulose phthalate, cellulose acetate phthalate or hydroxypropylmethylcellulose phthalate.

These pharmaceutical compositions may be in the form of granules or fine granules which may be prepared by adding to the active ingredient of the present invention a binder such as starch, gelatin, gum arabic, methylcellulose, sodium carboxymethylcellulose, heavy silicic anhydride or light silicic anhydride, followed by kneading and granulation by usual methods; or as a powder of the active ingredient of the present invention by itself; or as capsules which may be prepared by adding to the active ingredient of the present invention an excipient such as lactose, starch or crystalline cellulose and/or a lubricant such as magnesium stearate, calcium stearate or talc, and filling the mixture into capsules.

A solution or suspension may be prepared by adding any diluent customarily, used in the art. For example, suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic composition may also further contain ordinary dissolving aids, buffers, pain-alleviating agents, art preservatives, and optionally coloring agents, fragrances, flavors, sweeteners and other pharmacologically active agents such are well known in the art.

Quantitative Formulae

NOTE: All *Calendula officinalis* referenced in Tables below were manufactured with *Calendula* 4:1 but can be substituted with *Calendula* 10:1, 20:1 or the like and Example 4 will be adjusted as needed to deliver an equivalent concentration. Ratio of other ingredients will remain.

The topical compositions of the wound healing composition may be made into a wide variety of product types such as, without limitation, liquids, lotions, powders, creams, salves, gels, milky lotions, sticks, sprays (e.g., pump spray), aerosols, ointments, pastes, mousses, dermal patches, controlled release devices, and other equivalent forms. Preferably, the wound healing compositions are offered in spray form. The topical compositions of the wound healing composition may comprise the extracts of the instant invention and at least one pharmaceutically acceptable carrier.

Example 1

Composition for Use as a Shield

| Wound Healing Composition (Example 1) - Ingredients | | | | | |
|---|---|---|---|---|---|
| | | Percentage by Weight | | | |
| Ingredient | Nom Qnty | Nom % weight | Variance | General Variance | Desired Variance |
| Calendula officinalis | 8 tsp | 2.6 | 0.5-5.0 | 1.5-3.6 | 2.0-3.1 |
| Methylparaben | ½ tsp | 0.17 | 0.05-0.5 | 0.75-0.35 | 0.1-0.3 |
| Potassium Sorbate | ½ tsp | 0.17 | 0.05-0.5 | 0.75-0.35 | 0.1-0.3 |
| Carbomer 940 | 1 tbsps | 1 | 0.25-3.0 | 0.5-1.5 | 0.75-1.25 |
| Triethanolamine (adjust pH to 5-8) | ⅝ tsp | 0.26 | 0.0-1.0 | 0.1-0.45 | 0.15-0.37 |
| Glycerin | 16 tsp | 5 | 2.5-8.5 | 3.0-7.0 | 4.0-6.0 |
| Distilled water | 16 oz | 28.5 | 20-42 | 23-34 | 26-31 |
| Sulfur | 32 oz | 62 | 40-70 | 45-67 | 59-65 |
| Tea tree oil | 1 tsp | 0.3 | 0.1-0.8 | 0.15-0.6 | 0.2-0.4 |
| Total | 0.00 | 100.00 | | | |

Method of Manufacture

Potassium sorbate is dissolved in hot water (120° F.) and then *Calendula officinalis* is added. It may be allowed to rest for period of time prior to straining through a sieve to remove large fibers and then filtered thru smaller pore sized filters to remove remaining particulates. Straining is a preferred method but may not be absolutely necessary. Before continuing, the amount of liquid *Calendula officinalis* is measured. (It needs to be 16 oz of volume before continuing on or the formulae should be adjusted based upon how much volume is present.).

The solution is reheated to approximately 120° F. Methylparaben, Carbomer 940 and glycerin are dissolved with a high shear mixer. The product is allowed to slowly cool while continuing compounding. Once mixed thoroughly, triethanolamine is slowly added while mixing (the pH is kept preferably at 6-7). Once the right consistency is achieved, the sieved sulfur (to break up agglomerates) is added to the batch and mixed well. The tea tree oil is added last and well mixed.

The sulfur may be sieved thru a screen to provide an easier application (talc may be added to impede agglomeration and promote flowablity of the sulfur for ease of application.

Example 2

Sample Composition to be Used for Burns and or Deep Wounds

Composition 1:
Wound Healing Composition (Example 2) - Ingredients

| Ingredient | Percentage by Weight | | | |
|---|---|---|---|---|
| | Nom % Wt. | Variance | General Variance | Desired Variance |
| Calendula officinalis | 8.5 | 4.0-20 | 6.0-15.0 | 7.6-11.5 |
| Methylparaben | 0.2 | 0.05-0.5 | 0.75-0.35 | 0.1-0.3 |
| Potassium Sorbate | 0.2 | 0.05-0.5 | 0.75-0.35 | 0.1-0.3 |
| Distilled water | 91.1 | 80-95 | 84-96 | 88-93.4 |

Composition 2:

Sulfur or sublimed sulfur used in as a fine powder.

Method of Manufacture:

Potassium sorbate is dissolved in hot water (120° F.) and then *Calendula officinalis* is added. It may be allowed to rest for period of time prior to straining through a sieve to remove large fibers. The solution is then filtered thru small pored filters to remove remaining particulates. Straining is a preferred method but may not be absolutely necessary.

As noted above, the formulations of the wound healing composition also include topical compositions, and, in a particular embodiment, a topical formulation for treating burns and wounds. As defined herein "treating skin burns" means modulating pain, inflammation, reddening, swelling of the skin, which may be accompanied by a rash or sores. For example, a solution containing *calendula* was applied to the sunburn and may be followed by the application of sulfur on a mammal and therapeutic benefit was noted.

Example 3

Composition for Use as Follows on for Burn Patients

Method of Manufacture
Wound Healing Composition (Example 3) - Ingredients

| Ingredient | Percentage by Weight | | | |
|---|---|---|---|---|
| | Nom % Wt. | Variance | General Variance | Desired Variance |
| Calendula officinalis | 8.5 | 4.0-20 | 6.0-15.0 | 7.6-11.5 |
| Methylparaben | 0.17 | 0.05-0.5 | 0.75-0.35 | 0.1-0.3 |
| Potassium Sorbate | 0.17 | 0.05-0.5 | 0.75-0.35 | 0.1-0.3 |
| Carbomer 940 | 1 | 0.25-3.0 | 0.5-1.5 | 0.75-1.25 |
| Triethanolamine (adjust pH to 5-8) | 0.3 | 0.0-1.0 | 0.1-0.45 | 0.15-0.37 |
| Glycerin | 5 | 2.5-8.5 | 3.0-7.0 | 4.0-6.0 |
| Distilled water | 53.56 | 40-70 | 45-62 | 49-58 |
| Sulfur | 31 | 26-36 | 28-34 | 29-33 |
| Tea tree oil | 0.3 | 0.1-0.8 | 0.15-0.6 | 0.2-0.4 |

Potassium sorbate is dissolved in hot water (120° F.) and then *Calendula officinalis* is added. It may be allowed to rest for a period of time prior to straining through a sieve to remove large fibers and then filtered through small pored filters to remove remaining particulates. Straining is a preferred method but may not be absolutely necessary. Before continuing, the amount of liquid *Calendula officinalis* is measured. (It needs to be 16 oz of volume before continuing on or the formulae should be adjusted based upon how much volume is present).

The solution is reheated to approximately 120° F. Methylparaben, Carbomer 940 and glycerin are dissolved with a high shear mixer. The product is allowed to slowly cool while continuing compounding. Once mixed thoroughly, triethanolamine is slowly added while mixing (the pH is kept at 6-7 and pH strips are used to control the value). Once the right consistency is achieved, the sieved sulfur (to break up agglomerates) is added to the batch and mixed well. The tea tree oil is added last and well mixed.

Since this formulation will be dosed to the eye, the solution should be sterile filtered or autoclaved for required time to meet sterility.

Preservative may be included that can be administered to the eye (benzoic acid). The use of *Calendula officinalis* with or without preservative as a liquid applied to a mammal's eye, such as horse, has also provided therapeutic benefit Example 4

Composition for Use in the Eye

Wound Healing Composition (Example 4) - Ingredients

| Ingredient | Percentage by Weight | | | |
|---|---|---|---|---|
| | Nom % Wt. | Variance | General Variance | Desired Variance |
| Calendula officinalis | 8.5 | 4.0-20 | 6.0-15.0 | 7-10 |
| Sterile water | 91.5 | 80-96 | 85-94 | 90-93 |

A large number of dairy cattle throughout the world are affected by a disease called Mastitis. Mastitis is the inflammation of breast tissue. *Staphylococcus aureus* is the most common etiological organism responsible, but Staphylococcus epidermidis and streptococci are occasionally isolated as well. The composition can be modified to treat Mastitis.

The utilization of a pharmaceutically acceptable composition comprising of between 1 to 25% in weight of *calendula* and 10% to 50% in weight of sublimed sulfur combined in a topically-acceptable carrier that treats different types of mastitis, acute clinical, hyperacute clinical, subacute clinical, subclinical, chronic, gangrenous, contagious, environmental udder or intra-mammary infections.

Example 5

Composition for Use in Treating Mastitis, Acute Clinical, Hyperacute Clinical, Subacute Clinical, Subclinical, Chronic, Gangrenous, Contagious, Environmental Udder or Intra-Mammary Infections Mastitis Treatment Composition (Example 5) - Ingredients

| Ingredient | Percentage by Weight | | | |
|---|---|---|---|---|
| | Nom % Wt. | Variance | General Variance | Desired Variance |
| Calendula officinalis | 6.9 | 3.0-16 | 6.0-15.0 | 7.6-11.5 |
| Methylparaben | 0.23 | 0.05-0.5 | 0.75-0.35 | 0.1-0.3 |
| Potassium Sorbate | 0.23 | 0.05-0.5 | 0.75-0.35 | 0.1-0.3 |
| Carbomer 940 | 1.14 | 0.25-3.0 | 0.5-1.7 | 0.95-1.25 |
| Triethanolamine (adjust pH to 5-8) | 1.14 | 0.0-2.0 | 0.3-1.9 | 0.6-1.7 |
| Glycerin | 4.58 | 2.2-7.0 | 3.0-6.0 | 3.5-5.5 |
| Distilled water | 57.21 | 40-70 | 45-62 | 49-58 |
| Sulfur | 28.6 | 15-55 | 20-45 | 25-35 |

The use of such media and agents for dermatologically active substances are well known in the art. Except insofar as any conventional media or agent is incompatible with the active ingredient, its use in the therapeutic compositions is contemplated. Supplementary active ingredients can also be incorporated into the wound healing composition 100.

The present invention provides a *calendula* composition at the appropriate dosage and dosing regimen to be administered to an animal to alleviate the negative effects of exercise-induced pulmonary hemorrhage or bleeding. In a preferred embodiment, the dosage is 1 mL per 200 lbs or 5 mL per 1000 lbs of body weight of the animal to which *calendula* is administered. The preferred administration is two to three times a day. Extracts from *Calendula officinalis* (preferably 4:1) are useful in pharmaceutical compositions (weight percent) of the active ingredient with a carrier or vehicle in the composition in about 0.01 to 99%, preferably 1 to 20% and more preferred, about 1 to 12%. The following are several formulations, Examples 6-8 for preferred embodiments containing plant extracts of *Calendula officinalis* solution of the present invention.

Bev's Equine Bleeders Answer (Example 6) - Ingredients

| Ingredient | Percentage by Weight | | | |
|---|---|---|---|---|
| | Nom (% Wt.) | % Wt. | Variance | General |
| Calendula officinalis | 10.2 | 4.0-20 | 5.0-14.0 | 8.2-12.2 |
| Methylparaben | 0.3 | 0.05-0.5 | 0.75-0.45 | 0.1-0.4 |

Bev's Equine Bleeders Answer (Example 6) - Ingredients -continued

| Ingredient | Percentage by Weight | | | |
|---|---|---|---|---|
| | Nom (% Wt.) | % Wt. | Variance | General |
| Potassium Sorbate | 0.3 | 0.05-0.5 | 0.75-0.45 | 0.1-0.4 |
| Distilled water | 89.2 | 80-95 | 82-96 | 87.2-92.2 |

Bev's Equine Bleeders Answer (Example 7) - Ingredients

| Ingredient | Percentage by Weight | | | |
|---|---|---|---|---|
| | Nom (% Wt.) | % Wt. | Variance | General |
| Calendula officinalis | 7.8 | 4.0-20 | 5.0-14.0 | 6.6-10.5 |
| Methylparaben | 0.3 | 0.05-0.5 | 0.75-0.45 | 0.1-0.4 |
| Potassium Sorbate | 0.3 | 0.05-0.5 | 0.75-0.45 | 0.1-0.4 |
| Distilled water | 91.6 | 80-95 | 84-96 | 88.6-93.6 |

Bev's Equine Bleeders Answer (Example 8) - Ingredients

| Ingredient | Percentage by Weight | | | |
|---|---|---|---|---|
| | Nom (% Wt.) | % Wt. | Variance | General |
| Calendula officinalis | 3.9 | 4.0-20 | 5.0-14.0 | 6.6-10.5 |
| Methylparaben | 0.3 | 0.05-0.5 | 0.75-0.45 | 0.1-0.4 |
| Potassium Sorbate | 0.3 | 0.05-0.5 | 0.75-0.45 | 0.1-0.4 |
| Distilled water | 95.5 | 88-98 | 90-98 | 93.5-97.5 |

The present invention provides a *calendula* composition at the appropriate dosage and dosing regimen to be administered to an animal to alleviate the negative effects of muscle pulls, joint, tendon and ligament stresses, hematomas, and strains. The formulation, as noted in Example 9, can be applied to the affected area until absorbed with or without bandages. It should be reapplied liberally a second time without rubbing.

Bev's Equine Joint Fix It (Example 9) - Ingredients

| Ingredient | Percentage by Weight | | | |
|---|---|---|---|---|
| | Nom (% Wt.) | % Wt. | Variance | General |
| Calendula officinalis | 7.8 | 4.0-20 | 5.0-14.0 | 6.6-10.5 |
| Methylparaben | 0.3 | 0.05-0.5 | 0.75-0.45 | 0.1-0.4 |
| Potassium Sorbate | 0.3 | 0.05-0.5 | 0.75-0.45 | 0.1-0.4 |
| Distilled water | 91.6 | 80-95 | 84-96 | 88.6-93.6 |

The present invention provides a *calendula* composition at the appropriate dosage and dosing regimen to be administered to an animal to alleviate the negative effects of inflammation due to stress, bruises or cuts to ankles, tendons, shins or knees. The composition, as noted in Example 10, should be applied liberally to the area, wrapped in cotton with four to five layers of plastic barely snug against the leg and finally covered with both a bandage and over bandage. The application should be applied daily or until swelling and inflammation subsides.

Bev's Equine Leg Sweat (Example 10) - Ingredients

| Ingredient | Percentage by Weight | | | |
|---|---|---|---|---|
| | Nom (% Wt.) | % Wt. | Variance | General |
| Calendula officinalis | 7.3 | 4.0-20 | 5.0-14.0 | 6.6-10.5 |
| Methylparaben | 0.23 | 0.05-0.5 | 0.75-0.45 | 0.1-0.4 |
| Potassium Sorbate | 0.23 | 0.05-0.5 | 0.75-0.45 | 0.1-0.4 |
| Distilled water | 82.65 | 80-95 | 84-96 | 88.6-93.6 |
| Carbomer | 4.1 | 1.0-8.0 | 2.0-7.0 | 3.0-6.0 |
| Triethanolamine* | 0.91 | 0.04-4.0 | 0.4-2.0 | 0.8-1.0 |
| Glycerin | 4.58 | 2.2-7.0 | 3.0-6.0 | 3.5-5.5 |

*can substitute sodium hydroxide to adjust pH.

The present invention provides a *calendula* and Gentian composition at the appropriate dosage and dosing regimen to be administered to improve the eating regimen of high performance animals. Gentian is added to the formulation to stimulate the appetite. The formulation, as noted in Example 11, can be applied to the administered orally at 5 mLs orally twice a day, morning and evening.

Bev's Equine Appetite Stimulator (Example 11) - Ingredients

| Ingredient | Percentage by Weight | | | |
|---|---|---|---|---|
| | Nom (% Wt.) | % Wt. | Variance | General |
| Calendula officinalis | 7.8 | 4.0-20 | 5.0-14.0 | 6.6-10.5 |
| Methylparaben | 0.3 | 0.05-0.5 | 0.75-0.45 | 0.1-0.4 |
| Potassium Sorbate | 0.3 | 0.05-0.5 | 0.75-0.45 | 0.1-0.4 |
| Distilled water | 90 | 80-95 | 84-96 | 88.6-93.6 |
| Gentian | 1.6 | 0.04-4.0 | 0.4-2.8 | 0.8-2.4 |

The present invention provides a *calendula* and chamomile composition at the appropriate dosage and dosing regimen to be administered for mammals methods of preventing and treating gastric ulceration in mammals. It contain chamomile which will help a mammal to cope with the stresses that occur on a daily basis The formulation, as noted in Example 12, can be administered orally at 5 mLs twice a day, morning and evening.

Bev's Equine Ulcer Resolve (Example 12) - Ingredients

| Ingredient | Percentage by Weight | | | |
|---|---|---|---|---|
| | Nom (% Wt.) | % Wt. | Variance | General |
| Calendula officinalis | 7.8 | 4.0-20 | 5.0-14.0 | 6.6-10.5 |
| Methylparaben | 0.3 | 0.05-0.5 | 0.75-0.45 | 0.1-0.4 |
| Potassium Sorbate | 0.3 | 0.05-0.5 | 0.75-0.45 | 0.1-0.4 |
| Distilled water | 90 | 80-95 | 84-96 | 88.6-93.6 |
| Chamomile | 1.6 | 0.04-4.0 | 0.4-2.8 | 0.8-2.4 |

Normally horses eliminate excess body heat and cool themselves through the evaporation of sweat. When a horse is unable to sweat, the condition is referred to as anhydrosis. Anhydrosis is most notable in places where there is a combination of high heat and humidity such as the American Gulf States. If a horse stops sweating, the animal will try and cool itself with panting. Unfortunately, panting is not an efficient method of cooling. Some horses can sweat normally and then without warning shut down sweating altogether. At rest, a horse that does not sweat may have a body temperature between 102-103 degrees and under exercise will have a dangerous body temperature between 105-108 degrees. When the body temperature exceeds 106 degrees, brain damage may occur.

To date, there is no cure for anhydrosis. There are anecdotal remedies that horsemen have employed to manage anhydrosis and these include adding coffee grounds, or lite salts (potassium chloride or sodium chloride), or adding beer to the feed. This is a potentially dangerous condition which can only be managed by moving the horse to a cooler, less humid climate or by restricting the physical activity during the hot and humid hours.

The present invention provides a *calendula* composition at the appropriate dosage and dosing regimen to be administered with all 12 cell salts, *Chinchona officinalis* and Petroleum to an animal to alleviate the negative effects of not sweating due to stress or strenuous activity in high heat and humid conditions. The composition, as noted in Example 13, should be dosed preferably in two to three times per day at 2-5 mL per 1100 lb horse.

Bev's Sweat Stimulator

| Ingredient | Nom (% Wt.) | Purpose |
|---|---|---|
| *Calendula officinalis* (4:1) | 1-10% | Stimulate Circulation and Induce Sweating |
| Vitamin C | 5-20% | Antioxidant |
| Petroleum 6C | 0.01-5% | Solubilizer/Carrier |
| Petroleum 30C | 0.01-5% | Solubilizer/Carrier |
| *Benzoicum acidum* 10X | 0.01-5% | Improve liver and Kidney function |
| *Berber vulgaris* 10X | 0.01-5% | Improve liver and Kidney function |
| *Bryonia* 10X | 0.01-5% | Improve liver and Kidney function |
| *Calcarea fluorica* 6X HPUS | 0.01-5% | Cellular Rebalance and Restore Muscle |
| *Calcarea phosphoric* 3X HPUS | 0.01-5% | Cellular Rebalance and Restore Muscle |
| *Calcarea suphurica* 3X HPUS | 0.01-5% | Cellular Rebalance and Restore Muscle |
| *Cantharis* 10X | 0.01-5% | Improve liver and Kidney function |
| *Carduus benedictus* 10X | 0.01-5% | Improve liver and Kidney function |
| *Carduus marianus* 3X | 0.01-5% | Improve liver and Kidney function |
| *Ceanothus americanus* 10X | 0.01-5% | Improve liver and Kidney function |
| *Chelidonium majus* 10X | 0.01-5% | Improve liver and Kidney function |
| *Chionathus virginica* 10X | 0.01-5% | Improve liver and Kidney function |
| *Cinchona officinalis* 10X | 0.01-5% | Stimulates Digestive Juices |
| *Cynara scolymus* 3X | 0.01-5% | Improve liver and Kidney function |
| *Dioscorea villosa* 10X | 0.01-5% | Improve liver and Kidney function |
| *Dolichos pruriens* 10X | 0.01-5% | Improve liver and Kidney function |
| *Ferrum phosphoricum* 3X HPUS | 0.01-5% | Cellular Rebalance and Restore Muscle |
| *Iris versicolor* 10X | 0.01-5% | Improve liver and Kidney function |
| *Juniperus communis* 10X | 0.01-5% | Improve liver and Kidney function |
| *Kali muraiticum* 3X HPUS | 0.01-5% | Cellular Rebalance and Restore Muscle |
| *Kali phosphoricum* 3X HPUS | 0.01-5% | Cellular Rebalance and Restore Muscle |
| *Kali sulphuricum* 3X HPUS | 0.01-5% | Cellular Rebalance and Restore Muscle |
| *Magnesia phosphoric* 3X HPUS | 0.01-5% | Cellular Rebalance and Restore Muscle |
| *Natrium muriaticum* 3X HPUS | 0.01-5% | Cellular Rebalance and Restore Muscle |

-continued

Bev's Sweat Stimulator

| Ingredient | Nom (% Wt.) | Purpose |
|---|---|---|
| Natrium phosporicum 3X HPUS | 0.01-5% | Cellular Rebalance and Restore Muscle |
| Nux vomica 10X | 0.01-5% | Improve liver and Kidney function |
| Ptelea trifoliata 10X | 0.01-5% | Improve liver and Kidney function |
| Silicea 6X HPUS | 0.01-5% | Cellular Rebalance and Restore Muscle |
| Solidago virgaurea 3X | 0.01-5% | Improve liver and Kidney function |
| Taraxacum officinale 10X | 0.01-5% | Improve liver and Kidney function |
| Uricum acidum 15X | 0.01-5% | Improve liver and Kidney function |
| Water | Q.S. | Diluent |

Wherein a range of values is provided, it is understood that each intervening value, to the tenth of the unit of the lower limit unless the context clearly dictates otherwise, between the upper and lower limit range and any other stated or intervening value in that stated range is encompassed within this invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

While the preferred embodiments of the invention have been described above, it will be recognized and understood that various modifications can be made in the invention and the appended claims are intended to cover all such modifications which may fall within the spirit and scope of the invention. For example, one skilled in the art can utilize any formulation as a carrier for the *calendula* and sulfur, such as gels, creams, salves, ointments, solutions, soaps, and dusting powders to carry the high concentrations of sulfur in combination with *calendula* to promote wound healing. The use of different pharmaceutical carrier is not important to the inventive step of using the preparation containing sulfur and *calendula* or sulfur, *calendula* and tea tree oil. It will therefore be readily understood by those individuals skilled in the art that the present invention is susceptible to a broad utility and application. Any equivalent embodiments are intended to be within the scope of this invention.

The following presents various exemplary applications of the wound healing composition 100.

Figure 2:
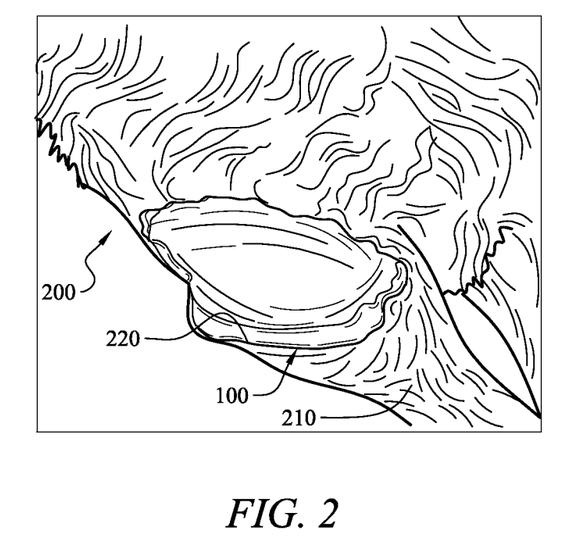
FIG. 2 presents an exemplary traumatic wound on an animal's leg.
Figure 3:
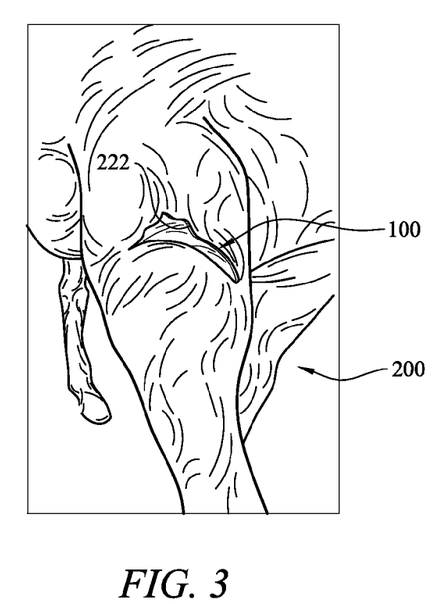
FIG. 3 presents the wound originally introduced in FIG. 2, wherein the wound has significant improvement following a short time span after application of the wound healing composition.
Figure 4:
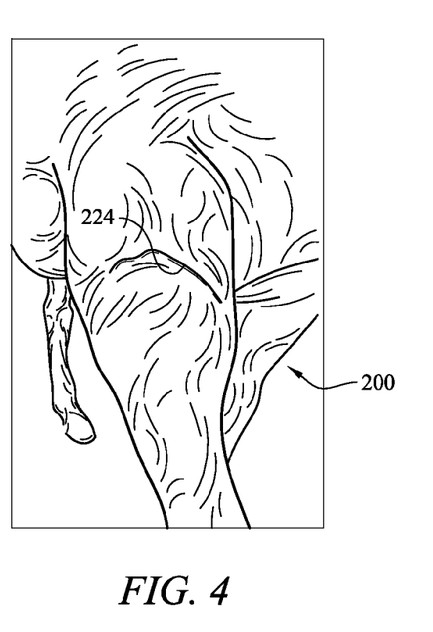
FIG. 4 presents the wound originally introduced in FIG. 2, wherein the wound has completely healed.

A first exemplary embodiment is presented in FIGS. 2 through 4, wherein an animal 200 has a first exemplary wound 220 on the leg 210 thereof. A caretaker initially identifies the first exemplary wound 220. The caretaker applies the wound healing composition 100 to the wound. The first exemplary wound 220 begins to heal transitioning from a fresh wound into a partially healed first exemplary wound 222. The first exemplary wound 220 continues to heal until becoming a completely healed wound 224.

Figure 5:
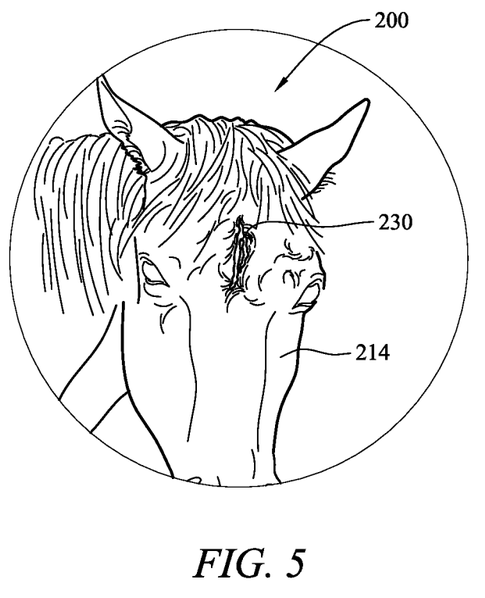
FIG. 5 presents a second exemplary wound.
Figure 6:
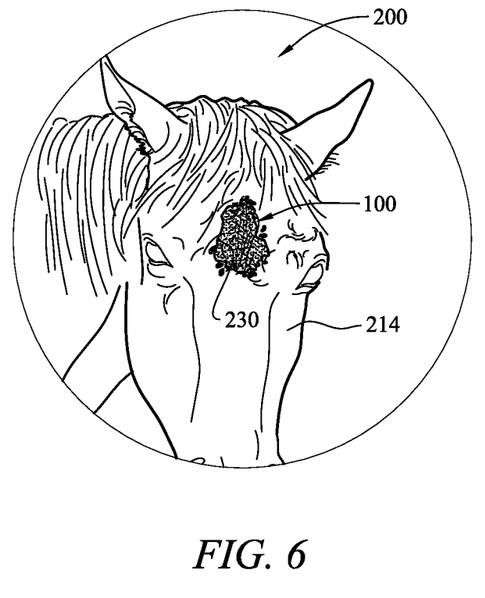
FIG. 6 presents the wound originally introduced in FIG. 5, wherein the wound has been covered by the wound healing composition.
Figure 7:
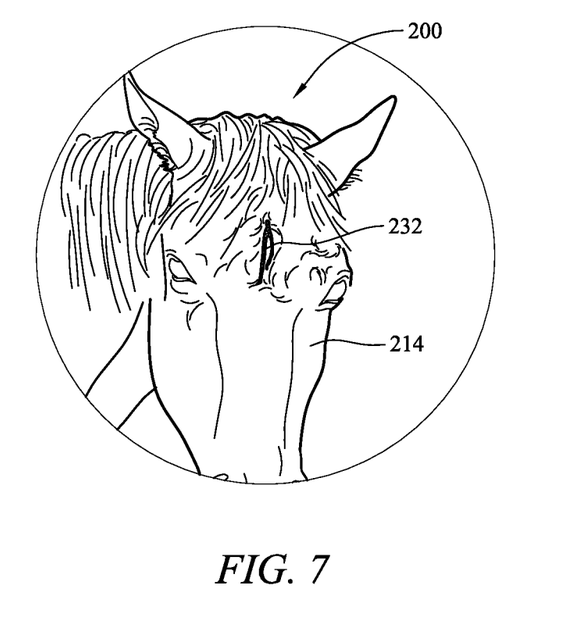
FIG. 7 presents the wound originally introduced in FIG. 5, wherein the wound is shown partially healed.

A second exemplary embodiment is presented in FIGS. 5 through 6, wherein an animal 200 has a second exemplary wound 230 on the head 214 thereof. A caretaker initially identifies the second exemplary wound 230. The caretaker applies the wound healing composition 100 to the wound as illustrated in FIG. 6. The applied wound healing composition 100 accelerates the healing process. The second exemplary wound 230 begins to heal, transitioning from a fresh wound into a partially healed second exemplary wound 232. It is understood that over time, the second exemplary wound 230 becomes completely healed (not shown).

Figure 8:
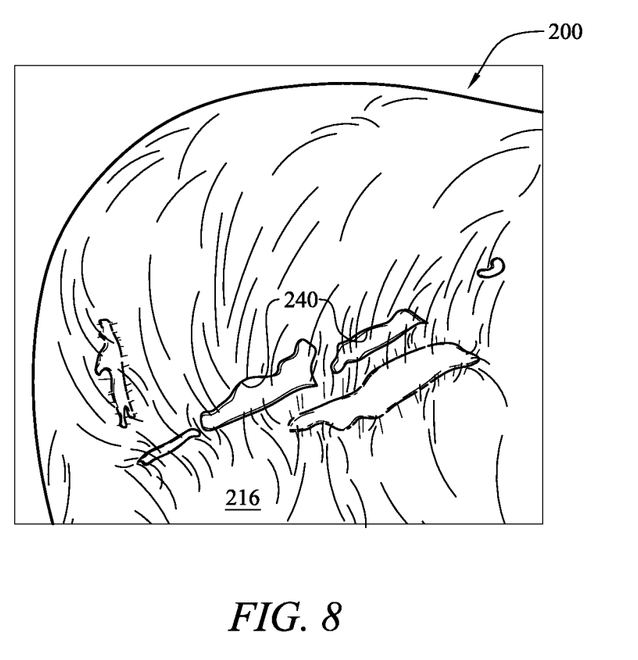
FIG. 8 illustrates a third exemplary wound.
Figure 9:
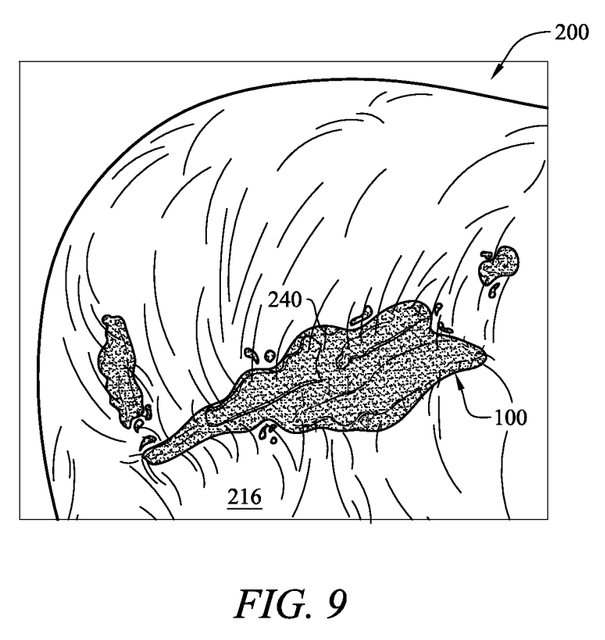
FIG. 9 presents the wound originally introduced in FIG. 8, wherein the wound has been covered by the wound healing composition.
Figure 10:
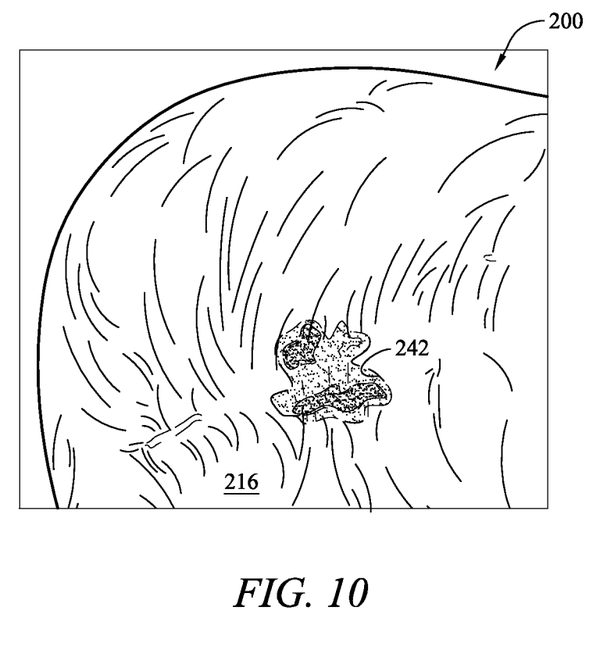
FIG. 10 presents the wound originally introduced in FIG. 8, wherein the wound is shown partially healed.

A third exemplary embodiment is presented in FIGS. 8 through 10, wherein an animal 200 has a third exemplary wound 240 on the torso 216 thereof. A caretaker initially identifies the third exemplary wound 240. The caretaker applies the wound healing composition 100 to the wound as illustrated in FIG. 9. The applied wound healing composition 100 accelerates the healing process. The third exemplary wound 240 begins to heal, transitioning from a fresh wound into a partially healed third exemplary wound 242. It is understood that over time, the third exemplary wound 240 becomes completely healed (not shown).

We claim:

1. A method for treatment of exercise-induced pulmonary hemorrhage (EIPH) in a mammal, comprising administering to the mammal identified as having a need for the treatment a pharmaceutically active preparation consisting essentially of an effective amount of *Calendula officinalis* in a pharmaceutically acceptable carrier.

2. The method of claim 1 wherein the mammal is selected from the group consisting of an equine specimen, a camel, and a dog.

3. The method of claim 1 wherein the pharmaceutically active preparation is administered orally to the mammal.

4. The method of claim 3 wherein the *Calendula officinalis* is present in an amount of between about 1% and about 12% of a total preparation weight.

5. A method for the treatment of a wound, burn or inflammation in a mammal identified as having a need for the treatment comprising administering to the mammal a pharmaceutically active preparation comprising an effective amount of *Calendula officinalis*, sulfur, and tea tree oil.

6. The method of claim 5, wherein the administering comprises applying an initial preparation of 2-20% by weight of *Calendula officinalis* in a solvent to the wound followed by the direct application of sulfur to the wound.

7. The method of claim 5, wherein the treatment comprises treating and/or impeding the progression of a burn, and wherein the administering comprises the stepwise addition of a first composition to a burned area, the composition comprising *calendula*, sulfur and tea tree oil initially applied to the burned area followed by treatment of a pharmaceutically acceptable composition to the burned area, the composition comprising about 1 to 25% by weight of *calendula*, 25% to 80% by weight of sublimed sulfur, and 0.05% to 5.0% by weight of tea tree oil in a topically-acceptable carrier.

8. The method of claim 5, wherein the composition comprises about 1 to about 25% by weight of *Calendula officinalis*, about 25% to about 80% by weight of sublimed sulfur, and about 0.05% to about 5.0% by weight of tea tree oil in a topically-acceptable carrier.

9. The method of claim 5, wherein the pharmaceutically active preparation further comprises:
 a preservative,
 a humectant,
 an essential oil,
 a gelling agent,
 a permeation enhancer, and
 one or more pH adjusting ingredients to adjust pH of the preparation to a pH of from 5 to 8.

10. A method for stimulating appetite in a mammal identified as having a need for the stimulating comprising administering to the mammal a pharmaceutically active preparation comprising an effective amount of *Calendula officinalis* and Genetian.

11. The method of claim 10 wherein the pharmaceutically active preparation comprises about 1 to about 25% in weight of *calendula* and about 0.04 to 4.0% in weight of Gentian in an orally acceptable carrier.

12. A method for treatment of gastric ulcers in a mammal identified as having a need for the treatment comprising administering to the mammal a pharmaceutically active preparation comprising an effective amount of *Calendula officinalis* and chamomile.

13. The method of claim 12 wherein the pharmaceutically active preparation comprises about 1 to about 25% by weight of *Calendula officinalis* and about 1% to about 5% by weight of chamomile in an orally acceptable carrier.

14. A method for treatment of anhydrosis in a mammal identified as having a need for the treatment comprising administering to the mammal a pharmaceutically active preparation comprising:

- an effective amount of *Calendula officinalis* with ascorbic acid; and
- about 1-5% by weight of each salt in the group consisting of *Calcarea fluorica, Calcarea phosphoric, Calcarea sulphurica, Ferrum phosphoricum, Kali muraiticum, Kali phosphoricum, Kali sulphurica, Magnesia phosphoric, Natrium muriaticum, Natrium phosphoricum, Natrium sulphuricum* and Silicea.

* * * * *